(12) United States Patent
Herbrechtsmeier et al.

(10) Patent No.: US 8,945,942 B2
(45) Date of Patent: Feb. 3, 2015

(54) **STABILIZATION OF BIO-SENSORS FOR *IN VIVO* APPLICATIONS**

(75) Inventors: Peter Herbrechtsmeier, Königstein (DE); Achim Müller, Grossostheim (DE); Monika Knuth, Aschaffenburg (DE); Katharina Nikolaus, Aschaffenburg (DE)

(73) Assignee: Eyesense AG, Basil (CH)

( * ) Notice: Subject to any disclaimer, the term of this patent is extended or adjusted under 35 U.S.C. 154(b) by 145 days.

(21) Appl. No.: 13/503,599

(22) PCT Filed: Oct. 25, 2010

(86) PCT No.: PCT/EP2010/066036
§ 371 (c)(1),
(2), (4) Date: Jun. 29, 2012

(87) PCT Pub. No.: WO2011/054690
PCT Pub. Date: May 12, 2011

(65) Prior Publication Data
US 2012/0258551 A1    Oct. 11, 2012

(30) Foreign Application Priority Data
Oct. 26, 2009    (EP) .................................... 09174054

(51) Int. Cl.
*G01N 33/66* (2006.01)
*C07K 14/42* (2006.01)

(52) U.S. Cl.
CPC .............. *C07K 14/42* (2013.01); *G01N 33/66* (2013.01); *Y10S 436/827* (2013.01)
USPC .......................... 436/501; 436/827; 435/283.1

(58) Field of Classification Search
CPC ............ A61K 39/00; A61K 2039/505; A61K 39/39591; C07K 2319/40; C07K 14/42; C12N 2760/16134; G01N 33/6845; G01N 2500/04; G01N 33/66; B82Y 15/00; B82Y 30/00; C08B 37/0024; C12P 21/02; C12P 17/02; C12P 7/24; C12P 7/40
See application file for complete search history.

(56) References Cited

U.S. PATENT DOCUMENTS 5,962,414 A    10/1999  Birk
2007/0249917 A1*  10/2007  Ballerstadt et al. ........... 600/316

FOREIGN PATENT DOCUMENTS

GB    1 488 988    10/1977

OTHER PUBLICATIONS

Schultz et al., Diabetes Care, 1982; 5:245-253.*
Smith et al., Plant Physiol 1982;vol. 70, p. 1199-1209.*
Blumberg et al.1976;Biochimia and Biophysica Acta,453:357-364.*
Ballerstadt et al., "Concanavalin A for in vivo glucose sensing: A biotoxicity review," *Biosensors and Bioelectronics*, vol. 22, pp. 275-284 (2006).
Campbell et al., "Biochemical Characterization of Canavalin, the Major Storage Protein of Jack Bean," *Plant Physiology*, vol. 70, pp. 1199-1209 (1982).
Carlini, et al. "Isolation and characterization of a toxic protein from *Canavalia ensiformis* (Jack Bean) seeds, distinct from concanavalin A" *Toxicon*, vol. 19, No. 5, pp. 667-675 (1981).
Chebotareva et al., "Biochemical Effects of Molecular Crowding," *Biochemistry*, vol. 69, pp. 1522-1536 (2004).
Jones et al., "Some proteins from the Jack Bean, *Canavalia ensiformis*" *Journal of Chemistry*, vol. 28, pp. 67-75 (1916).
Kamra et al., "Reaction of concanavalin A with dimethyl adipimidate: purification and of a crosslinked concanavalin a derivative with enhanced thermal stability," *Biochimica Et Biophsica Acta*, vol. 966, No. 2, pp. 181-187 (1988).
Matto et al., "Entrapment of porous and stable concanavalin A-peroxidase complex into hybrid calcium alginate-pectin gel," *Journal of Chemical Technology and Biotechnology*, vol. 81, pp. 1316-1323 (2006).
Russell et al., "A Fluorescence-Based Glucose Biosensor Using Concanavalin A and Dextran Encapsulated in a Poly(ethylene glycol) Hydrogel," vol. 71, No. 15, pp. 3126-3132 (1999).
International Search Report cited in related International Patent Application No. PCT/EP2010/066036, completed Jan. 31, 2011.
International Preliminary Report on Patentability prepared for related International Patent Application No. PCT/EP2010/066036. completed Aug. 18, 2011.
International Preliminary Report on Patentability issued in related International Patent Application No. PCT/EP2010/066036, dated Jun. 14, 2012.

* cited by examiner

*Primary Examiner* — Shafiqul Haq
*Assistant Examiner* — Carmencita M Belei
(74) *Attorney, Agent, or Firm* — Foley & Lardner LLP

(57) ABSTRACT

The present invention relates to the use of preparations for stabilizing isolated proteins. In particular, the use of such a preparation for stabilizing receptors in biochemical sensors is disclosed. The invention in addition relates to biochemical sensors containing such preparations.

7 Claims, No Drawings

STABILIZATION OF BIO-SENSORS FOR *IN VIVO* APPLICATIONS

The present invention relates to the use of preparations for stabilizing isolated proteins. In particular, the use of such a preparation for stabilizing receptors in biochemical sensors is disclosed. The invention in addition relates to biochemical sensors containing such preparations.

It is frequently desirable for technical application of proteins to free them from interfering impurities. An important field of use of purified proteins is biochemical sensors. Proteins which are used as receptors of biochemical sensors must have a high affinity for the analyte. In order to detect the binding of the analyte to the receptor, the receptor is frequently modified in order to make the interaction of analyte and receptor measurable. A targeted modification is made difficult and frequently impossible by impurities. Therefore, proteins are extracted from natural cells and tissues and purified.

However, the purification of proteins has the disadvantage that the stability of the isolated protein is frequently lower than its stability in the natural environment. The addition of chaperones, amino acids, proteins (e.g. BSA), polysaccharides or polysaccharide derivatives frequently increases the stability of isolated proteins. Often, low- or high-molecular-weight additives are used in order to decrease the free volume in the solution ("molecular crowding"). In this case, proteins, polysaccharides or synthetic polymers can be used. From the prior art, in particular polyethylene glycol, Ficoll, dextran, ribonuclease and bovine serum albumin are known. The effect of these additions can be clarified by the effect of the " excluded volume" (Chebotareva et al., 2004, Biochemical Effects of Molecular Crowding, Biochemistry (Moscow), 69: 1522-1536).

An object of the invention is therefore provision of preparations which make possible an improved stabilization of isolated proteins. The object is achieved by the embodiments which are described in the patent claims and hereinafter.

The invention therefore relates to the use of a cell lysate fraction for stabilizing an isolated protein, wherein the cell lysate fraction is produced by a method that comprises the steps:
a) producing the cell lysate from cells; and
b) separating off the isolated protein from the cell lysate, whereby the cell lysate fraction for stabilizing the isolated protein is obtained.

Preferably, the isolated protein and the cell lysate fraction are produced from *Canavalia ensiformis*. Particularly preferably, the cell lysate fraction contains precanavalin. Preferably, the cell lysate fraction is further processed after the isolated protein is separated off. Preferably, the the isolated protein is a receptor, very particularly preferably concanavalin A. Preferably, the isolated protein is a component of a biochemical sensor. Particularly preferably, the biochemical sensor in addition comprises dextran and concanavalin in hydrogel particles.

The cell lysate fraction which is used according to the invention is obtainable by a method for providing a cell lysate fraction stabilizing an isolated protein comprising the steps
  a) producing the cell lysate from the cells; and
  b) separating off the protein to be isolated from the cell lysate.

"Cells" in this application is taken to mean all prokaryotic or eukaryotic cells which express the protein that is to be isolated. This includes genetically transformed cells in which the protein that is to be isolated is expressed in a recombinant manner. The cells can be present as individual cells of a prokaryotic or eukaryotic cell culture or in the form of a tissue sample of an animal or plant organism or of a fungus.

Methods for producing a cell lysate are well known to those skilled in the art. The cells can be disrupted in the scope of the method according to the invention using all known mechanical or non-mechanical disruption methods. Preferred mechanical disruption methods are homogenization using rotating blades (in animal cells), the Potter-Elvehjem method, milling of the cells or the tissue, the grinding in a mortar with sand, aluminum oxide or glass beads, cell disruption by cavitation forces in the case of ultrasound, and pressing a cell suspension at high pressure through a narrow valve (e.g. in a French Press). Those skilled in the art know that, in mechanical disruption methods, heat can be formed, in such a manner that, in many cases temperature control is necessary in order to prevent denaturation of the proteins. Preferred non-mechanical disruption methods are repeated freezing and thawing of the cells, treating the cells with hypotonic solutions, treatment with lysozyme in the case of Gram-positive bacteria, treatment with EDTA and subsequent incubation with lysozyme in the case of Gram-negative bacteria or treatment with toluene in the case of yeasts. Of course, various members of said methods can be combined with one another or with other disruption methods which are not mentioned here.

During the disruption, the proteins must be protected from harmful influences. Preferably, cold or specific inhibitors are used in order to prevent the breakdown of the proteins by proteases. For protection of thiol groups, preferably reducing agents are used, particularly preferably dithiothreitol or dithioerythol. For protection from heavy metal ions, ethylenediaminetetraacetic acid (EDTA) is preferred. This also binds divalent cations which can activate proteases. For prevention of the aggregation of proteins, preferably non-ionic detergents are used.

Preferably, the disruption method and any protective measures optionally to be taken are not only adapted to the desired protein being present in active form in the cell lysate, but the components of the cell lysate which mediate the stabilization of the protein must also not be functionally impaired by the disruption method chosen.

Before practical use thereof, isolated proteins are in many cases modified. For instance, receptors for use in biochemical sensors are frequently labeled. This labeling proceeds via covalent modification of the receptor, for example using fluorescent dyes. In order that the modified isolated protein which is to be stabilized is not diluted by the non-modified protein present in the cell lysate fraction, it is preferred to separate off from the cell lysate the protein that is to be isolated. The expression "separating off the protein that is to be isolated from the cell lysate" designates purification of the desired protein. As a result, at least one cell lysate fraction is present which contains the protein as isolated protein. In addition, separately therefrom, at least one cell lysate fraction is present which does not contain the abovementioned protein or contains it only in a minor extent. The isolated protein is separated from the natural context thereof, i.e. from the molecules with which it was present in the cell lysate. Preferably, the isolated protein is present at least 50%, at least 75%, at least 80%, at least 90%, at least 95%, or, particularly preferably, at least 99% (weight/weight) pure, based on the molecules from the natural environment thereof. The cell lysate fraction which contains the isolated protein can contain molecules in any desired amount which do not originate from the natural environment of said protein, but were added in the course of purification, or after purification. One example thereof would be components of the buffer used.

Methods for separating off from a cell lysate a protein that is to be isolated are known to those skilled in the art. Preferred methods are precipitation and differential solubilization, ultracentrifugation, chromatographic methods and electrophoresis.

The precipitation of proteins is preferably achieved by adding ammonium sulfate in increasing concentrations. Protein fractions of different solubility precipitate out in this method successively depending on the ammonium sulfate concentration reached and can be separated off. Equally preferred is precipitation of the protein by acidification of the medium using a suitable buffer.

Ultracentrifugation is based on the principle that, in the gravitational field generated by the centrifugation, particles sediment more rapidly the denser and more compact they are. As a consequence of the equilibrium between centrifugal force and buoyancy which is established during a sufficiently long centrifugation, the individual proteins accumulate at the points in the vessel at which buoyancy and centrifugal force balance one another. Use of sucrose gradients can facilitate this process.

The chromatographic isolation of proteins is based on the principle that the proteins dissolved in a mobile phase, preferably a buffer, migrate over a stationary phase. The phases are selected in such a manner that the interaction of differing strength of individual proteins from the protein mixture with the solid phase leads to running times of different length of the individual protein fractions over the stationary phase. In what way proteins and stationary phase interact depends on the type of chromatography. Preferred chromatographic methods for isolating proteins are size-exclusion chromatography (based on the differing size of the proteins that are to be separated), affinity chromatography (based on the ability of individual proteins to bind specifically to the column material), ion-exchange chromatography (based on the differing isoelectric points of various proteins) and reverse-phase chromatography (based on the differing hydrophobicity of various proteins).

The expression " isolated protein" , in the scope of this patent application, designates any proteins in which there is interest in the isolation thereof in the functional state. Hereinafter, the expression "desired protein" is used synonymously. Isolated proteins in the context of the present application preferably comprise enzymes, receptors, modulatory proteins, transcription factors, cytoskeletal proteins, binding proteins and membrane transporters, particularly preferably receptors. Very particularly preferably, the protein isolated is concanavalin A. The isolated proteins, in the scope of the method, can be present as pure substances or in partially isolated form. Preferably, isolated proteins or preparations of isolated proteins comprise less than 50%, less than 25%, less than 10%, less than 5%, less than 1%, or less than 0.5%, protein or protein and cellular components as impurity.

"Enzyme" is taken to mean any protein which is able to catalyze a chemical reaction. In this process it is of no importance whether, in the context of the chemical reaction, other molecules are converted or whether the enzyme acts autocatalytically.

A "receptor" is any protein which is able to bind specifically a molecule, the ligand, and to react to this binding with a conformational change or an activity change. Proteins which in their natural state display no reaction to the binding of a ligand can also be chemically modified in such a manner that the binding of a ligand leads to measurable changes in the protein. In addition, through the combination of a fluorescently-labeled receptor with a likewise fluorescently-labeled ligand, competitive assays are possible. In the absence of unlabeled ligands in the sample, only the fluorescently-labeled ligand binds to the receptor. The spatial vicinity of the two fluorescent dyes influences their light emission. If unlabeled ligand is then present in a sample, the unlabeled ligand displaces the fluorescently-labeled ligand from the receptor and thus changes the light emission of the system. The change in light emission of the system therefore depends on the amount of unlabeled ligand which is introduced into the system with the sample and displaces labeled ligands from the receptors. Specific binding means that the ligand is bound with a significantly higher affinity than other substances. Preferably, the ligand is bound with at least 10-fold, 100-fold, 1000-fold, 10 000-fold or 100 000-fold higher affinity than other ligands. Ligands are preferably ions, small molecules, nucleic acids (DNA or RNA in single- or double-stranded form) or other proteins of any length. Small molecules can belong to any known class of molecules. They are preferably lipids, fatty acids, purines, pyrimidines, sugars, alkaloids, amino acids, biogenic amines, isoprenoids or steroids. Particularly preferably, the small molecule is a sugar, very particularly preferably glucose. Particularly preferably, the receptor is a lectin, very particularly preferably concanavalin A.

Lectins are proteins which are able to bind carbohydrate structures specifically. They participate in many types of molecular and cellular recognition processes in animals, plants and bacteria and have no enzymatic function. Many lectins are post-translationally modified by glycosyl radicals.

Concanavalin A is a lectin which can bind α-D-glucose and similar sugars without reacting them enzymatically. The monomer consists of 237 amino acids and contains manganese and calcium. At neutral pH it forms a tetramer which decomposes in the acidic range into two dimers. It occurs at particularly high concentration in the jack-bean *Canavalia ensiformis*. Concanavalin A preferably has the amino acid sequence defined by SEQ ID NO: 3.

In this application, those proteins are designated "modulatory proteins" which interact with other proteins and thereby change the activity of these proteins. The consequence can be a reduced activity of the interaction partner (inhibition) or an increased activity (activation). The binding partner of the modulator is preferably an enzyme. In this case, the binding of the modulator affects the affinity for the substrate or the velocity of the enzymatic reaction of the substrate. Equally preferably, the binding partner is a receptor. In this case, the modulator can act agonistically, i.e. can activate the receptor by binding to it, or the modulator can bind to the receptor as an antagonist, without activating it in the course of this. Further preferably, the binding partner is a transcription factor. In this case, the binding of the modulator affects the ability of the transcription factor to modify gene expression for its part.

A "transcription factor" in the context of this application is a protein, the activity of which consists of promoting or inhibiting the expression of one or more genes in the cell.

"Binding proteins" are proteins which are able to bind other molecules (ligands) specifically. Specific binding means that the ligand is bound with significantly higher affinity than other substances. Preferably, the ligand is bound with at least 10-fold, 100-fold, 1000-fold, 10 000-fold or 100 000-fold higher affinity than other ligands.

The expression " membrane transporters" is taken to mean those proteins which enable or facilitate the passage of other molecules through the cell membrane. These proteins are localized in the cell membrane.

Cytoskeletal proteins are proteins which stabilize the spatial structure of a cell and, in combination with motor proteins, mediate cellular movement processes. Cytoskeletal proteins are preferably actin, intermediary filaments and microtubules. Motor proteins associated with actin filaments and microtubules are preferably kinesin, dynein and myosin.

The term " stabilization" denotes the maintenance of the structure and/or the function of an isolated protein. Since the structure of a protein is a substantial precondition for the function thereof, stabilization of the protein structure preferably leads to maintenance of the function of the protein. The protein structure that is to be stabilized is preferably the structure that the protein has in its natural environment, i.e. in the tissue or in the cell. The preparation according to the invention preferably stabilizes the secondary, tertiary or quaternary structure of the isolated protein. Stabilization in the context of this invention is taken to mean the stabilization of a statistically significant proportion of the molecules of the isolated protein. For instance, the recovery rate of functional isolated protein after depletion of the preparation according to the invention is preferably at least 50%, at least 75%, at least 80%, at least 90%, at least 95%, or, particularly preferably, at least 99%. The recovery rate can therefore be determined as the proportion of functional molecules of the isolated protein of the total amount of molecules of the isolated protein after addition of the preparation according to the invention and storage. Preferably, for measuring the recovery rate, the activities of the preparation containing the isolated protein are compared immediately before or after addition of the preparation according to the invention and at a later time point. Furthermore, comparisons are made with preparations of the isolated protein without addition of the preparation according to the invention at the same time points.

The present invention advantageously makes possible the improved stabilization of isolated proteins, in particular receptors. As Example 5 shows, concanavalin A is stabilized better by the non-binding cell lysate fraction from the seeds of *Canavalia ensiformis* than by bovine serum albumin which is known in the prior art as a stabilizer for proteins. A further surprising advantage of the cell lysate fraction according to the invention that stabilizes an isolated protein is the possibility of autoclaving this cell lysate fraction without the activity thereof being impaired. For applications in the medical field of the cell lysate fraction according to the invention stabilizing an isolated protein, this is a considerable advantage, since the freedom from germs of the cell lysate fraction can be ensured in this manner.

In a preferred embodiment of the present invention, the isolated protein and the cell lysate fraction stabilizing the isolated protein are produced from the seed of the jack-bean (*Canavalis ensiformis*).

In a particularly preferred embodiment of the present invention, the cell lysate fraction stabilizing the isolated protein contains precanavalin. If the cell producing the protein that is to be isolated does not contain, or does not contain sufficient, precanavalin in its natural form, it is preferred to express precanavalin in this cell in a recombinant manner. The addition of precanavalin to a cell lysate is likewise preferred.

The term "precanavalin" denotes a protein contained in the seed of the jack-bean (*Canavalla ensiformis*). Precanavalin monomers, in gel electrophoresis under denaturing conditions, display a molecular weight of 49 000 Daltons. Trypsin splits precanavalin into two peptides of 24 000 and 25 000 Daltons molecular weight each. Under conditions which permit crystallization of these cleavage products, the larger of the two peptides is cleaved a second time by trypsin (Campbell Smith et al., 1982, Biochemical Characterization of Canavalin, the Major Storage Protein of Jack Bean, Plant Physiology, 70: 1199-1209). Preferably, canavalin has an amino acid sequence as defined in SEQ ID NO: 2. In a preferred embodiment of the present invention, the precanavalin has a sequence identity of at least 60%, 70%, 80%, 90%, 95%, 97%, 98% or 99% with the amino acid sequence defined by SEQ ID NO: 2. Preferably, precanavalin is encoded by a polynucleotide having the sequence defined by SEQ ID NO: 1. A method for providing purified precanavalin from the jack-bean is described in Example 1.

In a further preferred embodiment of the present invention, the cell lysate fraction stabilizing an isolated protein is processed further.

This workup preferably comprises adding protease inhibitors and/or binding free metal ions by chelators. In addition, sterilization of the cell lysate fraction stabilizing the protein is preferred. Very particularly preferably, the workup comprises the enrichment of a subpopulation of components stabilizing particularly effectively the isolated protein in the cell lysate fraction. Likewise, very particular preference is given to separating off interfering components from the cell lysate fraction. Such a separation of the cell lysate fraction stabilizing the protein is used in order to remove from said cell lysate fraction those molecules which hinder the industrial application of the protein. For isolating a subpopulation of molecules from the cell lysate fraction stabilizing the protein, all methods known to those skilled in the art for separating mixtures of molecules can be used. Preferably, those separation methods are used which were described above for the purification of proteins.

In the context of the study underlying the present invention, it has been found that precanavalin is particularly highly suitable for stabilizing isolated proteins. Therefore, the further workup of the cell lysate fraction stabilizing an isolated protein is preferably the enrichment of precanavalin.

Precanavalin is preferably enriched by a method which comprises the following steps:
1. suspension of jack-bean meal in a suitable buffer;
2. chromatographic separation of the concanavalin A using a Superdex 200 column. The precanavalin is located in the non-binding fraction;
3. dialysis of the non-binding fraction against water;
4. lyophilization of the non-binding fraction;
5. admixing the non-binding fraction with acidic precipitation buffer, preferably 50 mM Na acetate, pH 4.4, and subsequent centrifugation;
6. washing the sediment with distilled water and subsequent centrifugation;
7. the remaining pellet is taken up in a suitable buffer, preferably 1% (weight/weight) NaCl and 0.1% (weight/weight) K2HPO4, pH 7.0, and centrifuged;
8. after the centrifugation the supernatant is collected;
9. the sediment remaining after the centrifugation is taken up in sodium chloride solution, preferably 5% (weight/weight) and centrifuged again;
10. the supernatant obtained in step 9 is combined with the supernatant from step 8;
11. dialysis of the combined supernatants against distilled water;
12. concentration of the precanavalin by acid-base extraction, preferably by precipitation using 1 N acetic acid, pH 5.1 and taking up the sediment in 0.01 N NaOH, wherein the pH after takeup in the base is not above 8.0;
13. dialysis against the application buffer provided for the subsequent ion-exchange chromatography, preferably 20 mM Tris, 100 mM NaCl, pH 7.2;
14. ion-exchange chromatography, preferably using a column of DEAE Sepharose FF and the application buffer mentioned in step 13, elution preferably with increasing salt gradient;
15. identification of the purest fractions, preferably using SDS-PAGE, combining these fractions;
16. dialysis against distilled water; and
17. freeze-drying the precanavalin.

Particularly preferably, precanavalin is enriched by a simplified method which comprises the steps:
1. suspension of jack-bean meal in a suitable buffer;
2. ion-exchange chromatography, preferably using a column of DEAE-Sepharose FF, elution preferably with increasing salt gradient;
3. identification of the purest fractions, preferably using SDS-PAGE, combination of these fractions;
4. dialysis against distilled water; and
5. freeze-drying the precanavalin.

A further preferred embodiment of the present invention relates to the use of a preparation containing precanavalin for stabilizing an isolated protein. Particular preference is given to the use of the abovementioned preparation for stabilizing concanavalin A.

A "preparation containing precanavalin" is preferably in liquid or solid form. Preferably, the preparation, apart from precanavalin, also contains other components from the cellular environment of the isolated protein. Equally preferably, the preparation contains chaperones, bovine serum albumin and/or compatible solutes. Further preferably, the preparation contains organic or inorganic buffer substances. Preservatives which suppress the growth of bacteria and fungi and wetting agents are also preferred as components of the preparation according to the invention. The weight fraction of precanavalin of the dry matter of the preparation according to the invention is preferably at least 30%, 40%, 50%, 60%, 70%, 80%, 90%, 95%, 97%, 98%, 99% or 99.5%.

In a preferred embodiment, the precanavalin contained in the preparation according to the invention is produced in a recombinant manner.

Methods for the recombinant preparation of proteins are well known to those skilled in the art. A nucleic acid sequence which encodes precanavalin is introduced into an expression vector which makes possible the expression of precanavalin in the selected host organism. For this it is preferred that the nucleic acid sequence which encodes precanavalin is under the control of a suitable regulatory sequence. Suitable regulatory sequences are, for example, the lac, trp or tac promotor for E. coli, the AOX1 or GAL-1 promotor for yeasts or the CaMV promotor for plants. For use in animal cells, the CMV, SV40, or RSV (Rous sarcoma virus) promoter and also the CMV enhancer, the SV40 enhancer or a globin-intron is preferred. Preferred expression vectors are plasmids, phages, retroviral vectors and artificial chromosomes. Preferred host organisms for the recombinant preparation of precanavalin are plants, prokaryotes and fungi, or else mammals. Plasmids are preferably introduced into the host cell by electroporation, precipitation using calcium phosphate or rubidium chloride, or by heat shock. Preferred methods for transformation of plant cells are ballistic inoculation and the transformation mediated by *Agrobacterium tumefaciens*.

The present invention further relates to a method for stabilizing an isolated protein comprising the addition of a precanavalin-containing preparation according to the invention to the isolated protein.

The addition of the precanavalin-containing preparation according to the invention to the desired protein makes possible the exact dosage of the preparation according to the invention. A defined and reproducible stabilization of the desired protein can be achieved in this manner. Preferably, the dried preparation is added as solid to the solution containing the desired protein and dissolved therein. Equally preferably, a stock solution of the preparation according to the invention is added to the solution containing the desired protein. Particular preference is given to incorporation of the precanavalin-containing preparation according to the invention into hydrogel particles, very particular preference to alginate beads, wherein the hydrogel particles also contain the isolated protein.

In a preferred embodiment of the method according to the invention, the isolated protein is a receptor, more preferably a lectin, and still more preferably concanavalin A.

The present invention further relates to the use of the cell lysate fraction according to the invention stabilizing an isolated protein for stabilizing an isolated protein, wherein said isolated protein is a component of a biochemical sensor.

A "biochemical sensor" contains a molecule, preferably a protein, which is able to bind with high affinity the substance that is to be detected. This protein is denoted hereinafter as "receptor". A biochemical sensor prepared according to the invention contains at least one receptor and also the molecules which are present in the cell lysate fraction stabilizing the receptor/the receptors. A person skilled in the art knows that a biochemical sensor can, in addition, contain other molecules.

The binding of the analyte to the receptor makes possible qualitative, and preferably also quantitative, detection of the analyte in a sample. Qualitative detection is taken to mean the observation of the presence or absence of the analyte in the sample. A person skilled in the art knows that qualitative detection, depending on the sensor used, has a lower limit of detection, i.e. the sample must have a defined minimum concentration of the analyte in order that the presence thereof can be established. Quantitative detection of the analyte in addition further delivers information on the amount or concentration of the analyte in the sample. In order to make the interaction between receptor and analytes measurable, it is preferred to modify the protein used chemically. Particular preference is given to modification of an isolated protein by labeling with fluorescent dyes.

The term "sample" denotes any liquid in which the analyte is to be detected. Preference is given to blood, plasma, serum, tear fluid, tissue fluid and urine, particular preference to the tissue fluid under the conjunctiva of the eye. Equally preferred are tissue samples. The sample is preferably present as a sample isolated from the body of the patient. More preferably, the sample is present at its natural location. In this case, the sensor is preferably introduced into the body of the patient and used directly at the site at which the sample is situated.

In a preferred embodiment of the invention, the biochemical sensor contains concanavalin A as receptor. Such biochemical receptors can be used for determining the glucose concentration in samples, since concanavalin A binds glucose. In this case, the biochemical sensor preferably contains hydrogels in addition to the receptor and the cell lysate fraction stabilizing the receptor. Preference is given to hydrogels of synthetic molecules, biomolecules or modified biomolecules. Preferred synthetic molecules are polyacrylates, polyacrylamides and polyvinyl alcohols. Preferred biomolecules are gelatin, carageenan, agarose, amylose, amylopectin, alginates, gellan, cellulose and cellulose derivatives. Particular preference is given to polyvinyl alcohols and alginate. If the biochemical sensor contains said hydrogels, receptor and analyte are present in heterogeneous phase.

In a particularly preferred embodiment, the biochemical sensor contains hydrogel particles in which the cell lysate fraction stabilizing the isolated protein, dextran and concanavalin A are present.

In addition, the present invention relates to the use of a cell lysate fraction according to the invention stabilizing an isolated protein or a precanavalin-containing preparation for preparing a biochemical sensor.

The invention also provides a biochemical sensor comprising an isolated protein and a cell lysate fraction stabilizing the isolated protein, as defined above. Preferably, the biochemical sensor comprises a receptor as isolated protein, particularly preferably concanavalin A. Preferably, the cell lysate fraction is contained together with dextran and the isolated protein, preferably the receptor, and particularly preferably concanavalin A, in hydrogel particles.

Likewise, the invention provides a biochemical sensor comprising concanavalin A and precanavalin. Preferably, the concanavalin A and the precanavalin are contained together with dextran in a hydrogel particle.

The exemplary embodiments hereinafter serve only to illustrate the invention. They are not intended to restrict in any way the subject matter of the patent claims.

EXAMPLES

Example 1

Production of the Non-binding Fraction of Jack-beans 300 g of jack-bean meal (Canavalia ensiformis) are suspended in 100 mM buffer and filtered for removal of membrane components. In total, 30 g of protein are applied to a Superdex 200 column and the protein fraction not binding to the column material is collected. In total, 3 liters of non-binding fraction (nbF) are obtained. The solution is dialyzed against water. Then freeze-drying (lyophilization) is performed. The lyophilized substance can be taken up in the working buffer.

Example 2

Purification of Precanavalin

Extraction of a Crude Fraction Precanavalin from the Non-binding Fraction 8.0 g of dialyzed and freeze-dried nbF is admixed with precipitation buffer (50 mM Na acetate, pH 4.4), incubated and then centrifuged. The sediment of the precipitation is washed with water and again centrifuged. The pellet is dissolved in 800 ml of salt-hydrogen phosphate solution (1% (w/v) NaCl+0.1% (w/v) $K_2HPO_4$, pH 7.0). The supernatant after centrifugation is collected. The sediment is dissolved in 500 ml of 5% strength sodium chloride solution and then centrifuged. The combined supernatants of the salt extractions are dialyzed against bidistilled water. The dialysate is centrifuged. The sediment is discarded and the supernatant is adjusted using 1N acetic acid to pH 5.1 for precipitation. The precipitation batch is incubated overnight and centrifuged on the next day. The sediment is taken up in 50 ml of 0.01N NaOH and admixed with 6 ml of 0.1N NaOH, in such a manner that a virtually clear solution is present. The pH is tested us should be no more than pH 8.0. The batch is incubated overnight at 4° C. The acid-base extraction step is repeated once. The basic precanavalin extract last obtained is dialyzed against 20 mM Tris buffer, 100 mM NaCl, pH 7.2.

Purification of Precanavalin

The precanavalin is purified via DEAE-anion exchange chromatography (DEAE Sepharose FF). The protein is applied to the column equilibrated with application buffer (20 mM Tris buffer, 100 mM NaCl, pH 7.2), subsequently washed with buffer until the base absorption line at 280 nm is stable and then eluted (elution buffer: 20 mM Tris buffer, 1 M NaCl, pH 7.2). The elution proceeds using a salt gradient of 0-100%. After analysis of the elution fractions by SDS-PAGE, the purest fractions are combined. The purified precanavalin is dialyzed overnight against bidistilled water and then freeze-dried.

Example 3

Preparation of Hydrogel Particles Containing Non-binding Fraction (or Precanavalin)

2 g of alginic acid, sodium salt and 8 g of non-binding fraction (or precanavalin) are dissolved in 200 g of water with stirring in a 250 ml conical flask. In a 5 L beaker, 66.2 g of $CaCl_2.2H_2O$ are dissolved in 4931.3 g of water.

The alginate/protein solution is conveyed via a pump into a two-fluid nozzle. At the same time, at the second entrance of the nozzle, compressed air is applied, in such a manner that the alginate/protein solution is atomized into fine droplets. The droplets are carried by the air flow into an ultrasonic bath containing the calcium chloride solution, where they gelate and sink to the bottom. The gelated balls are then collected and optionally autoclaved.

Example 4

In vitro Stability Test of Glucose Sensors

Glucose sensors are stored in each case in 1 ml of physiological buffer at 37° C. After an appropriate storage time, the glucose sensor is removed and the fluorescence spectrum determined at various glucose concentrations. The change in fluorescence intensities with increasing glucose content serves as a measure of the quality of the glucose sensor. Sensors of different storage times are compared with non-stored sensors and the absolute and percentage decrease in the reaction to glucose over the storage time is determined.

Table 1 shows comparatively the sensor response of sensors stabilized with non-binding fraction and with precanavalin in the physiological glucose range from 50 to 250 mg/dl, expressed as the percentage signal change per mg/dl increase in glucose concentration. Non-binding fraction and precanavalin give identical results.

TABLE 1

Storability of stabilized glucose sensors

| Stabilizer | Sensor response in the physiological glucose range between 50 and 250 mg/dl glucose after various storage times [signal change/mg/dl glucose] | | |
|---|---|---|---|
| | 14 days | 60 days | 120 days |
| non-binding fraction | 0.46 | 0.29 | 0.22 |
| Precanavalin | 0.44 | 0.29 | 0.20 |

Example 5

Result of the Stability Test Using Various Possible Stabilizers Relative to Non-stabilized Sensor Table 2 shows values after 120 days of storage under physiological conditions. Whereas known stabilizers such as BSA, HSA do not stabilize the sensor system, a marked stabilization is achieved by non-binding fraction from bean meal extract (also autoclaved).

TABLE 2

Comparison of various stabilizers

| Stabilizer | Improvement in sensor response after 120 days' storage in comparison with non-stabilized system |
|---|---|
| HSA | 2% |
| BSA | -3% |
| non-binding fraction | 41% |
| autoclaved non-binding fraction | 27% |

The invention claimed is:

1. A method for maintaining the function of concanavalin A in a biochemical sensor comprising contacting the concanavalin A with a cell lysate fraction comprising precanavalin, wherein the cell lysate fraction comprising precanavalin is produced by a method comprising the steps:

(a) producing the cell lysate from cells; and (b) separating the concanavalin A from the cell lysate, thereby obtaining the cell lysate fraction comprising precanavalin for maintaining the function of the concanavalin A, and wherein the cell lysate fraction comprising precanavalin as compared to known stabilizers improves the stability of the concanavalin A.

2. The method of claim 1, wherein the concanavalin A and the cell lysate fraction comprising precanavalin are produced from *Canavalia ensiformis.*

3. The method of claim 1, wherein the cell lysate fraction comprising precanavalin is further processed after the concanavalin A is separated from the cell lysate comprising precanavalin.

4. The method of claim 1, wherein the cell lysate fraction comprising precanavalin and the concanavalin A are components of a biochemical sensor and the concanavalin A binds with high affinity to the substance that is to be detected.

5. The method of claim 4. wherein the biochemical sensor additionally comprises dextran and concanavalin A in hydrogel particles.

6. A biochemical sensor comprising concanavalin A that binds with high affinity to a substance that is to be detected and a cell lysate fraction comprising precanavalin, wherein the cell lysate fraction comprising precanavalin is in contact with concanavalin A to maintain the function of concanavalin A.

7. The biochemical sensor of claim 6, wherein the cell lysate fraction comprising precanavalin is present together with d

SEQUENCE LISTING

<160> NUMBER OF SEQ ID NOS: 3

<210> SEQ ID NO 1
<211> LENGTH: 1403
<212> TYPE: DNA
<213> ORGANISM: Canavalia ensiformis

<400> SEQUENCE: 1

| | | | | | |
|---|---|---|---|---|---|
| attttgtatt | tagtaaacca | atatggcttt | ttctgcgcga | tttccactat | ggttattgct | 60 |
| gggagttgtt | ttgcttgctt | cagtttctgc | gtcgtttgcg | cactcgggac | acagtggagg | 120 |
| agaagcagag | gacgagagtg | aagagtcacg | ggcacaaaat | aacccgtatc | tctttaggtc | 180 |
| caacaagttc | ctcactctct | tcaagaacca | acacggttct | cttcgtctcc | tccaaaggtt | 240 |
| caacgaagac | accgagaaac | tggagaatct | tcgagactac | cgagttcttg | aatattgctc | 300 |
| caaaccaaac | accctccttc | tccctcacca | ctccgattct | gatcttctcg | tccttgtcct | 360 |
| cgagggacaa | gccatacttg | ttttggtgaa | ccctgacggc | agagacactt | acaaacttga | 420 |
| ccaaggcgat | gctatcaaaa | tccaagcagg | gacccctttc | tatctcatta | acccagacaa | 480 |
| caaccagaac | ctcagaatat | aaagttcgc | cataaccttc | aggagaccgg | gcacagtcga | 540 |
| ggatttcttc | ctatctagca | ctaaaagact | gccatcctac | ctgagtgcgt | tcagcaagaa | 600 |
| ttttctagag | gcctcctacg | attccccata | tgacgagata | gagcagactc | tgttgcaaga | 660 |
| agaacaagag | ggagtgatag | tcaaaatgcc | aaaggatcag | atccaggaaa | taagcaaaca | 720 |
| tgcccaatct | agctccagaa | aaacactttc | ttcccaagat | aaaccattta | acttgagaag | 780 |
| ccgagacccc | atctattcca | caactatgg | caagttatat | gagatcactc | cagagaaaaa | 840 |
| ctcacagcta | cgggacttgg | atatcctcct | caattgttta | caaatgaatg | agggagctct | 900 |
| ttttgtgcca | cactacaatt | caagggccac | agtcatactg | gtggctaatg | aaggaagagc | 960 |
| agaggttgag | ttggtgggtc | tagaacagca | acaacagcaa | ggattagaaa | gtatgcaact | 1020 |
| gcggaggtac | gctgccacgt | tatctgaagg | cgatataatc | gtaattccct | cgtcttttcc | 1080 |
| ggttgccctc | aaagctgctt | cagatctaaa | tatggttggg | attggtgtca | atgctgaaaa | 1140 |
| taacgagagg | aacttccttg | caggtcacaa | agagaacgtg | ataaggcaga | tacctaggca | 1200 |
| agtgagtgat | cttacattcc | ctggatctgg | tgaagaggtt | gaggagttat | tagagaatca | 1260 |
| aaaggaatcc | tactttgtgg | atggtcagcc | taggcatatt | gacgctggtg | gaaaggctag | 1320 |
| aagggcccat | ctgcctaatc | ttttccgcac | tttttactga | ataaactatc | taagttacta | 1380 |
| aataaaatgc | tgtaaaagca | aag | | | | 1403 |

<210> SEQ ID NO 2
<211> LENGTH: 445
<212> TYPE: PRT
<213> ORGANISM: Canavalia ensiformis

<400> SEQUENCE: 2

Met Ala Phe Ser Ala Arg Phe Pro Leu Trp Leu Leu Leu Gly Val Val
1               5                   10                  15

Leu Leu Ala Ser Val Ser Ala Ser Phe Ala His Ser Gly His Ser Gly
            20                  25                  30

Gly Glu Ala Glu Asp Glu Ser Glu Ser Arg Ala Gln Asn Asn Pro
        35                  40                  45

Tyr Leu Phe Arg Ser Asn Lys Phe Leu Thr Leu Phe Lys Asn Gln His
    50                  55                  60

Gly Ser Leu Arg Leu Leu Gln Arg Phe Asn Glu Asp Thr Glu Lys Leu

| | | | | | | | | | | | | | | | |
|---|---|---|---|---|---|---|---|---|---|---|---|---|---|---|---|
| | | | | 65 | | | | | 70 | | | | 75 | | 80 |

Glu Asn Leu Arg Asp Tyr Arg Val Leu Glu Tyr Cys Ser Lys Pro Asn
            85                  90              95

Thr Leu Leu Leu Pro His His Ser Asp Ser Asp Leu Leu Val Leu Val
            100                 105             110

Leu Glu Gly Gln Ala Ile Leu Val Leu Val Asn Pro Asp Gly Arg Asp
            115                 120             125

Thr Tyr Lys Leu Asp Gln Gly Asp Ala Ile Lys Ile Gln Ala Gly Thr
130                 135                 140

Pro Phe Tyr Leu Ile Asn Pro Asp Asn Asn Gln Asn Leu Arg Ile Leu
145                 150                 155             160

Lys Phe Ala Ile Thr Phe Arg Arg Pro Gly Thr Val Glu Asp Phe Phe
                165                 170             175

Leu Ser Ser Thr Lys Arg Leu Pro Ser Tyr Leu Ser Ala Phe Ser Lys
            180                 185             190

Asn Phe Leu Glu Ala Ser Tyr Asp Ser Pro Tyr Asp Glu Ile Glu Gln
            195                 200             205

Thr Leu Leu Gln Glu Glu Gln Glu Gly Val Ile Val Lys Met Pro Lys
210                 215                 220

Asp Gln Ile Gln Glu Ile Ser Lys His Ala Gln Ser Ser Ser Arg Lys
225                 230                 235             240

Thr Leu Ser Ser Gln Asp Lys Pro Phe Asn Leu Arg Ser Arg Asp Pro
            245                 250             255

Ile Tyr Ser Asn Asn Tyr Gly Lys Leu Tyr Glu Ile Thr Pro Glu Lys
            260                 265             270

Asn Ser Gln Leu Arg Asp Leu Asp Ile Leu Leu Asn Cys Leu Gln Met
            275                 280             285

Asn Glu Gly Ala Leu Phe Val Pro His Tyr Asn Ser Arg Ala Thr Val
290                 295                 300

Ile Leu Val Ala Asn Glu Gly Arg Ala Glu Val Glu Leu Val Gly Leu
305                 310                 315             320

Glu Gln Gln Gln Gln Gln Gly Leu Glu Ser Met Gln Leu Arg Arg Tyr
            325                 330             335

Ala Ala Thr Leu Ser Glu Gly Asp Ile Val Ile Pro Ser Ser Phe
            340                 345             350

Pro Val Ala Leu Lys Ala Ala Ser Asp Leu Asn Met Val Gly Ile Gly
            355                 360             365

Val Asn Ala Glu Asn Asn Glu Arg Asn Phe Leu Ala Gly His Lys Glu
370                 375                 380

Asn Val Ile Arg Gln Ile Pro Arg Gln Val Ser Asp Leu Thr Phe Pro
385                 390                 395             400

Gly Ser Gly Glu Glu Val Glu Glu Leu Leu Glu Asn Gln Lys Glu Ser
                405                 410             415

Tyr Phe Val Asp Gly Gln Pro His Ile Asp Ala Gly Gly Lys Ala
            420                 425             430

Arg Arg Ala His Leu Pro Asn Leu Phe Arg Thr Phe Tyr
435                 440                 445

<210> SEQ ID NO 3
<211> LENGTH: 290
<212> TYPE: PRT
<213> ORGANISM: Canavalia ensiformis

<400> SEQUENCE: 3

-continued

```
Met Ala Ile Ser Lys Lys Ser Ser Leu Phe Leu Pro Ile Phe Thr Phe
1             5                   10                  15

Ile Thr Met Phe Leu Met Val Val Asn Lys Val Ser Ser Ser Thr His
            20                  25                  30

Glu Thr Asn Ala Leu His Phe Met Phe Asn Gln Phe Ser Lys Asp Gln
            35                  40                  45

Lys Asp Leu Ile Leu Gln Gly Asp Ala Thr Thr Gly Thr Asp Gly Asn
    50                  55                  60

Leu Glu Leu Thr Arg Val Ser Ser Asn Gly Ser Pro Gln Gly Ser Ser
65                  70                  75                  80

Val Gly Arg Ala Leu Phe Tyr Ala Pro Val His Ile Trp Glu Ser Ser
                85                  90                  95

Ala Val Val Ala Ser Phe Glu Ala Thr Phe Thr Phe Leu Ile Lys Ser
                100                 105                 110

Pro Asp Ser His Pro Ala Asp Gly Ile Ala Phe Phe Ile Ser Asn Ile
            115                 120                 125

Asp Ser Ser Ile Pro Ser Gly Ser Thr Gly Arg Leu Leu Gly Leu Phe
    130                 135                 140

Pro Asp Ala Asn Val Ile Arg Asn Ser Thr Thr Ile Asp Phe Asn Ala
145                 150                 155                 160

Ala Tyr Asn Ala Asp Thr Ile Val Ala Val Glu Leu Asp Thr Tyr Pro
                165                 170                 175

Asn Thr Asp Ile Gly Asp Pro Ser Tyr Pro His Ile Gly Ile Asp Ile
            180                 185                 190

Lys Ser Val Arg Ser Lys Lys Thr Ala Lys Trp Asn Met Gln Asn Gly
            195                 200                 205

Lys Val Gly Thr Ala His Ile Ile Tyr Asn Ser Val Asp Lys Arg Leu
    210                 215                 220

Ser Ala Val Val Ser Tyr Pro Asn Ala Asp Ser Ala Thr Val Ser Tyr
225                 230                 235                 240

Asp Val Asp Leu Asp Asn Val Leu Pro Glu Trp Val Arg Val Gly Leu
                245                 250                 255

Ser Ala Ser Thr Gly Leu Tyr Lys Glu Thr Asn Thr Ile Leu Ser Trp
            260                 265                 270

Ser Phe Thr Ser Lys Leu Lys Ser Asn Glu Ile Pro Asp Ile Ala Thr
            275                 280                 285

Val Val
290
```